US011933750B2

(12) United States Patent
Okai et al.

(10) Patent No.: US 11,933,750 B2
(45) Date of Patent: Mar. 19, 2024

(54) CERAMIC MEMBER UNIT AND SENSOR PROVIDED WITH SAME

(71) Applicant: NGK SPARK PLUG CO., LTD., Nagoya (JP)

(72) Inventors: Masana Okai, Nagoya (JP); Kouji Matsuo, Nagoya (JP); Daisuke Tahira, Nagoya (JP)

(73) Assignee: NITERRA CO., LTD., Nagoya (JP)

( * ) Notice: Subject to any disclaimer, the term of this patent is extended or adjusted under 35 U.S.C. 154(b) by 666 days.

(21) Appl. No.: 16/972,903

(22) PCT Filed: Feb. 8, 2019

(86) PCT No.: PCT/JP2019/004621
§ 371 (c)(1),
(2) Date: Dec. 7, 2020

(87) PCT Pub. No.: WO2019/234972
PCT Pub. Date: Dec. 12, 2019

(65) Prior Publication Data
US 2021/0247339 A1    Aug. 12, 2021

(30) Foreign Application Priority Data

Jun. 8, 2018   (JP) ................................. 2018-110022

(51) Int. Cl.
*G01N 27/00* (2006.01)
*G01M 15/10* (2006.01)
(Continued)

(52) U.S. Cl.
CPC .......... *G01N 27/00* (2013.01); *G01M 15/102* (2013.01); *G01N 27/12* (2013.01); *G01N 27/407* (2013.01);
(Continued)

(58) Field of Classification Search
CPC .... G01N 27/00; G01N 27/12; G01N 27/4077; G01N 27/407; G01N 33/0009; G01N 33/0031; G01M 15/102
(Continued)

(56) References Cited

U.S. PATENT DOCUMENTS

| 5,688,390 A | * | 11/1997 | Yamauchi | .......... G01N 27/4077 |
| | | | | 204/426 |
| 6,851,180 B2 | * | 2/2005 | Hattori | ............... G01N 27/4062 |
| | | | | 73/23.31 |

(Continued)

FOREIGN PATENT DOCUMENTS

| CN | 105745532 A | * | 7/2016 | ......... G01N 27/4078 |
| DE | 102014222561 A1 | * | 5/2015 | ......... G01N 27/4078 |

(Continued)

OTHER PUBLICATIONS

Communication dated Aug. 22, 2022 issued by the State Intellectual Property Office of P.R. China in counterpart Chinese application No. 201980039057.3.

(Continued)

*Primary Examiner* — Clayton E. LaBalle
*Assistant Examiner* — Kevin C Butler
(74) *Attorney, Agent, or Firm* — Sughrue Mion, PLLC

(57) ABSTRACT

A ceramic member unit includes at least insertion members and a ceramic member having insertion sections into which the insertion members are inserted respectively. Each of the insertion sections has at least an insertion opening which opens on a deeper side of an introduction opening in the surface of the ceramic member while communicating with the introduction opening and into which the insertion member can be inserted. The insertion section further has taper hole portions becoming narrower toward the insertion opening in a communication region between the introduction (Continued)

opening and the insertion opening. The taper hole portions are connected to the insertion opening while increasing in a taper angle toward the insertion opening.

2 Claims, 14 Drawing Sheets

(51) Int. Cl.
    *G01N 27/12* (2006.01)
    *G01N 27/407* (2006.01)
    *G01N 33/00* (2006.01)

(52) U.S. Cl.
    CPC ..... *G01N 27/4077* (2013.01); *G01N 33/0009* (2013.01); *G01N 33/0031* (2013.01)

(58) Field of Classification Search
    USPC ........................................................ 73/31.05
    See application file for complete search history.

(56) References Cited

U.S. PATENT DOCUMENTS

| | | | | |
|---|---|---|---|---|
| 7,329,836 | B2 * | 2/2008 | Suzuki | F23Q 7/001 219/270 |
| 7,340,942 | B2 * | 3/2008 | Matsuo | G01N 27/407 73/31.05 |
| 8,047,051 | B2 * | 11/2011 | McCauley | G01N 27/4078 73/23.31 |
| 9,429,322 | B2 * | 8/2016 | Doi | H01T 13/08 |
| 9,644,842 | B2 * | 5/2017 | Harada | F02P 19/00 |
| 10,393,715 | B2 * | 8/2019 | Yonezu | G01N 33/0009 |
| 10,585,061 | B2 * | 3/2020 | Oba | H01R 13/26 |
| 10,989,686 | B2 * | 4/2021 | Mihara | G01N 27/4062 |
| 11,668,461 | B2 * | 6/2023 | Haussner | F23Q 7/001 219/270 |
| 2010/0050740 | A1 * | 3/2010 | Matsubara | G01N 27/4077 73/23.31 |
| 2017/0089808 | A1 * | 3/2017 | Hino | G01M 15/102 |
| 2019/0285578 | A1 * | 9/2019 | Mihara | G01N 27/4077 |
| 2021/0247339 | A1 * | 8/2021 | Okai | G01M 15/102 |

FOREIGN PATENT DOCUMENTS

| | | | | | |
|---|---|---|---|---|---|
| DE | 102016118236 | A1 | * | 3/2017 | .......... G01M 15/102 |
| JP | 08-193971 | A | | 7/1996 | |
| JP | 08193971 | A | * | 7/1996 | .......... G01N 27/407 |
| JP | 3588842 | B2 | * | 11/2004 | .......... G01N 27/407 |
| JP | 2005-134345 | A | | 5/2005 | |
| JP | 2005134345 | A | * | 5/2005 | |
| JP | 3713134 | B2 | * | 11/2005 | .......... G01N 27/407 |
| JP | 4538155 | B2 | * | 9/2010 | |
| JP | 4639515 | B2 | * | 2/2011 | .......... G01N 27/4077 |
| JP | 4863139 | B2 | * | 1/2012 | |
| JP | 4936132 | B2 | * | 5/2012 | |
| JP | 2013104832 | A | * | 5/2013 | .......... G01N 27/4077 |
| JP | 5592336 | B2 | * | 9/2014 | .......... G01N 27/4077 |
| JP | 2015099110 | A | * | 5/2015 | .......... G01N 27/4078 |
| JP | 2015-132471 | A | | 7/2015 | |
| JP | 2015132471 | A | * | 7/2015 | |
| JP | 2016-001106 | A | | 1/2016 | |
| JP | 2016001106 | A | * | 1/2016 | .......... G01N 27/409 |
| JP | 2019211413 | A | * | 12/2019 | .......... G01M 15/102 |
| JP | 6796403 | B2 | * | 12/2020 | |
| JP | 7183335 | B2 | * | 12/2022 | |
| JP | 7251527 | B2 | * | 4/2023 | .......... G01M 15/102 |
| WO | 2015/190518 | A1 | | 12/2015 | |
| WO | WO-2015190518 | A1 | * | 12/2015 | .......... G01N 27/409 |
| WO | WO-2022014282 | A1 | * | 1/2022 | .......... G01M 15/02 |

OTHER PUBLICATIONS

International Search Report (PCT/ISA/210) dated Apr. 23, 2019 issued by the International Searching Authority in International Application No. PCT/JP2019/004621.

* cited by examiner

CERAMIC MEMBER UNIT AND SENSOR PROVIDED WITH SAME

CROSS REFERENCE TO RELATED APPLICATIONS

This application is a National Stage of International Application No. PCT/JP2019/004621, filed Feb. 8, 2019, claiming priority based on Japanese Patent Application No. 2018-110022, filed Jun. 8, 2018.

TECHNICAL FIELD

The present invention relates to a ceramic member unit composed of, for example, lead wires, a separator, etc., and a sensor having the same.

BACKGROUND ART

An air-fuel ratio sensor and an oxygen sensor for detecting the concentration of oxygen in exhaust gas are known as gas sensors for improving the fuel efficiency of and controlling combustion in an internal combustion engine such as an automobile engine.

In a widely used gas sensor of this type, electrode portions such as electrode pads are provided on a rear-end portion of a plate-shaped sensor element, and lead wires are connected to the electrode portions, respectively, to output sensor output signals from the sensor element to. the outside (Patent Document 1).

The gas sensor can be manufactured as follows. First, as shown in FIG. 10A, an outer casing unit 700 is assembled by sequentially fixing a separator 500 and a rubber cap 52 to the interior of an outer casing 25 from a forward-end side. Then, lead wires 11 to 14 are inserted from their distal ends into respective insertion openings 52b of the rubber cap 52 located at the rear end of the outer casing unit 700 and then into respective insertion openings 500b of the separator 500.

Subsequently, as shown in FIG. 10B, covering materials located distally of cuts 11c to 14c are removed from distal ends of the lead wires 11 to 14 to expose core wires 11a to 14a. To the core wires 11a to 14a, unillustrated connection terminals are respectively connected by crimping. Next, the lead wires 11 to 14 are pulled rearward at their proximal side to accommodate the connection terminals in the insertion openings 500b, respectively, of the separator 500.

Further, the outer casing unit 700 with the lead wires 11 to 14 inserted therethrough is joined to an element unit (not shown) separately assembled beforehand, thereby completing the sensor.

PRIOR ART DOCUMENT

Patent Document

Patent Document 1: Japanese Patent Application Laid-Open (kokai) No. 2015-132471 (FIG. 4)

SUMMARY OF THE INVENTION

Problem to be Solved by the Invention

Incidentally, as shown in FIG. 11A, the separator 500 has one-step taper hole portion 500t located on a surface side of the insertion opening 500b. The taper hole portion 500t becomes narrower with depth so as to guide the insertion of the lead wire 11. In the course of insertion of the lead wire 11 into the insertion opening 500b, a distal end 11f of the lead wire 11 comes into contact with the taper hole portion 500t at a contact point P. Then, when the lead wire 11 is further pressed toward a deeper side, while being guided by the taper hole portion 500t, the distal end 11f of the lead wire 11 moves radially inward toward the insertion opening 500b as indicated by the arrow.

However, in the case of a soft insertion member such as the lead wire 11, as shown in FIG. 11B, as a result of the distal end 11f of the lead wire 11 being caught by the taper hole portion 500t, the lead wire 11 may bend and slip off to the outside from the insertion opening 500b as indicated by the arrow F; i.e., further insertion toward a deeper side may become difficult.

As shown in FIG. 12, the above-mentioned taper hole portion 500t is formed as follows: ceramic powder is pressed into a separator green compact 500x, and the green compact 500x is fired. In forming the green compact 500x by pressing, a pin 1100 is inserted into the powder to form the insertion opening 500b, and a die 1200 having a sharp edge portion 1200e is disposed around the pin 1100 and pressed for forming the taper hole portion 500t. At this time, the edge portion 1200e may break as a result of exposure to sliding movement of the die and compaction pressure of the powder.

Accordingly, as shown in FIG. 13, there is provided a technique for providing a flat land portion 500f at the edge portion of a die 1210 to prevent the breakage of the edge portion of the die 1210. In this case, as shown in FIG. 14, the yielded separator 500 has the horizontal portion 500f formed between the taper hole portion 500t and the insertion opening 500b.

However, in the course of insertion of the lead wire 11 into the insertion opening 500b of the separator 500, the distal end 11f of the lead wire 11 is caught by the horizontal portion 500f located on the deeper side of the taper hole portion 500t, resulting in difficulty in further insertion. Since the horizontal portion 500f does not slope radially inward in contrast to the taper hole portion, the distal end 11f in contact with the horizontal portion 500f is not guided radially inward; therefore, further insertion toward a deeper side fails.

Accordingly, an object of the present invention is to provide a ceramic member unit allowing smooth insertion of an insertion member into an insertion opening thereof and providing improved insertability, and a sensor having the same.

Means for Solving the Problem

In order to solve the above problem, a ceramic member unit according to a first aspect of the present invention comprises at least an insertion member, and a ceramic member having an insertion section into which the insertion member is inserted. The ceramic member unit is characterized in that: the insertion section has at least an insertion opening which opens on a deeper side of an introduction opening in a surface of the ceramic member while communicating with the introduction opening and into which the insertion member can be inserted; the insertion section further has a taper hole portion in a region through which the introduction opening and the insertion opening communicate with each other, the taper hole portion becoming narrower toward the insertion opening; and the taper hole portion is connected to the insertion opening while increasing in taper angle toward the insertion opening.

In the case where the ceramic member is fixed in terms of the maximum diameter of the introduction opening, the maximum diameter of the insertion opening, and the depth from the introduction opening to the insertion opening, a taper hole portion that increases in taper angle toward the insertion opening is always smaller (shallower) in taper angle than a one-step taper hole portion. That is, the taper hole portion is always located radially outward of the one-step taper hole portion.

Accordingly, when the insertion member is inserted into the insertion section of the ceramic member, the distal end of the insertion member initially comes into contact with the taper hole portion of the present invention at a contact point located deeper (closer to the insertion opening) than a contact point at which the distal end of the insertion member initially comes into contact with the one-step taper hole portion. As a result, the insertion member in a state (start state) in which the insertion member has been inserted more deeply in the insertion section is inserted further deeply. Therefore, even if the insertion member bends to some extent, the insertion member is restrained from slipping off to the outside from the insertion opening and can be smoothly inserted further deeply into the insertion opening, whereby insertability improves.

Since a deeper-side portion of the taper hole portion is also tapered, as compared with the case where a horizontal portion is connected to the insertion opening, the distal end of the insertion member can be restrained from being caught.

A ceramic member unit according to a second aspect of the present invention comprises at least an insertion member, and a ceramic member having an insertion section into which the insertion member is inserted. The ceramic member unit is characterized in that: the insertion section has at least an insertion opening which opens on a deeper side of an introduction opening in a surface of the ceramic member while communicating with the introduction opening and into which the insertion member can be inserted; the insertion section further has a straight portion and a deeper-side taper hole portion in this order from the introduction opening in a region through which the introduction opening and the insertion opening communicate with each other; the straight portion extends from the introduction opening toward the insertion opening; and the deeper-side taper hole portion is connected to the insertion opening while becoming narrower from the straight portion toward the insertion opening.

In the case where the ceramic member is fixed in terms of the maximum diameter of the introduction opening, the maximum diameter of the insertion opening, and the depth from the introduction opening to the insertion opening, a shape having the straight portion and the deeper-side taper hole portion toward the insertion opening is such that the straight portion is always located radially outward of the one-step taper hole portion and such that the deeper-side taper hole portion is always smaller (shallower) in taper angle than the one-step taper hole portion. That is, the straight portion and the deeper-side taper hole portion are always located radially outward of the one-step taper hole portion.

Accordingly, when the insertion member is inserted into the insertion section of the ceramic member, the distal end of the insertion member initially comes into contact with the deeper-side taper hole portion of the present invention at a contact point located deeper (closer to the insertion opening) than a contact point at which the distal end of the insertion member initially comes into contact with the one-step taper hole portion. As a result, the insertion member in a state (start state) in which the insertion member has been inserted more deeply in the insertion section is inserted further deeply. Therefore, even if the insertion member bends to some extent, the insertion member is restrained from slipping off to the outside from the insertion opening and can be smoothly inserted further deeply into the insertion opening, whereby insertability improves.

Since the deeper-side taper hole portion is also tapered, as compared with the case where a horizontal portion is connected to the insertion opening, the distal end of the insertion member can be restrained from being caught.

In the ceramic member unit of the present invention, the insertion section may form a through hole extending from the insertion opening toward a deeper side.

The present ceramic member unit also allows application to the insertion section having a through hole.

A sensor of the present invention comprises the ceramic member unit according to claim 3 and a sensor element extending in a direction of an axial line. In the sensor, the ceramic member is a ceramic member, and the insertion member is the lead wire to be electrically connected to the sensor element.

Effects of the Invention

According to the present invention, the insertion member can be smoothly inserted into the insertion opening of the ceramic member, whereby insertability can be improved.

MODES FOR CARRYING OUT THE INVENTION

An embodiment of the present invention will next be described.

Figure 1:
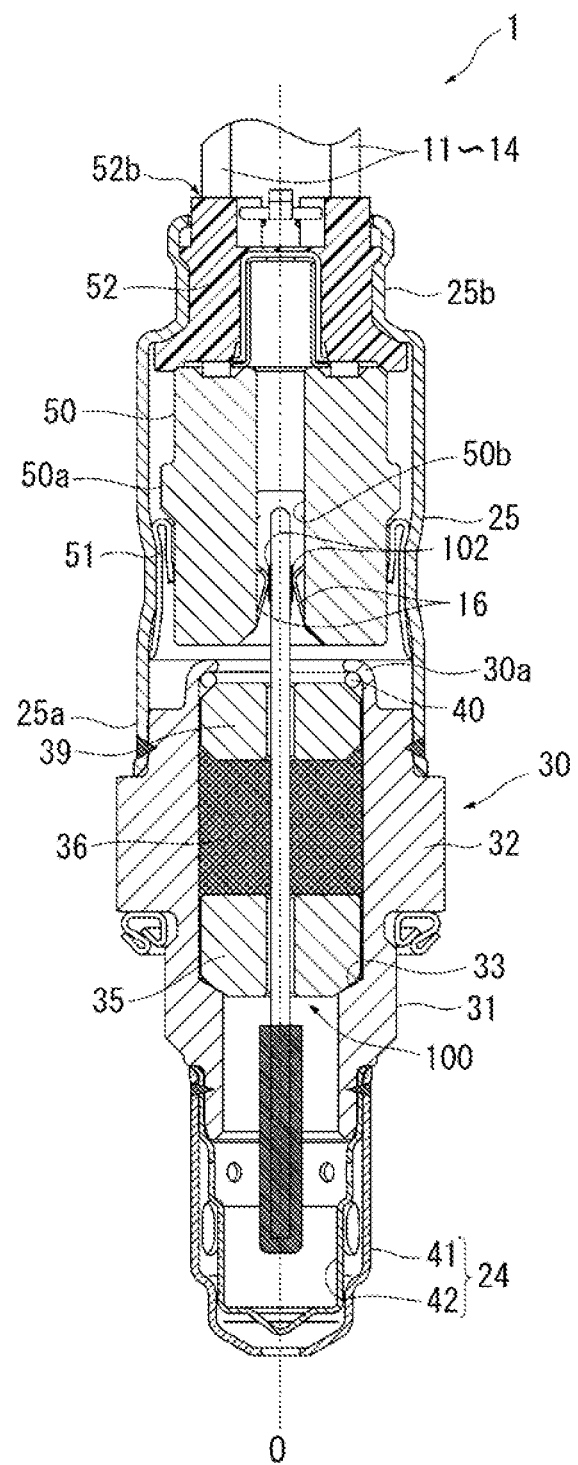
FIG. 1 is an overall sectional view of a sensor according to an embodiment of the present invention taken along a longitudinal direction.

FIG. 1 is an overall sectional view of a sensor (oxygen sensor) 1 according to an embodiment of the present invention taken along a longitudinal direction.

The sensor 1 is an oxygen sensor for detecting the concentration of oxygen in exhaust gas from automobiles and various internal combustion engines.

As shown in FIG. 1, the sensor 1 has a plate-shaped sensor element 100, a metallic shell 30 that holds therein the sensor element 100, etc., a protector 24 attached to a forward end portion of the metallic shell 30, as well as lead wires 11 to 14, an outer casing 25, a separator 50, and a rubber cap (elastic member) 52, which will be described later, etc. The sensor element 100 is disposed in such a manner as to extend in a direction of an axial line O.

The lead wires 11 to 14 and the separator 50 correspond to the "insertion member" and the "ceramic member," respectively, in the claims. An assembly of the lead wires 11 to 14 and the separator 50 corresponds to the "ceramic member unit" in the claims.

The metallic shell 30 is made of SUS430 and has an externally threaded portion 31 adapted to mount the gas sensor to an exhaust pipe, and a hexagonal portion 32 to which a mounting tool is fitted in mounting the gas sensor. The metallic shell 30 further has a shell-side stepped portion 33, which projects radially inward. A ceramic holder 35 and a talc 36 are disposed, in this order from the forward-end side, on the shell-side steeped portion 33. A sleeve 39 made of alumina is disposed on the rear-end side of the talc 36, and the sensor element 100 is inserted through an axial hole of the sleeve 39. A rear-end crimp portion 30a of the metallic shell 30 is bent inward to press the sleeve 39 toward the forward-end side of the metallic shell 30 through a ring member 40 made of stainless steel.

As a result of pressing of the sleeve 39, the talc 36 is compressively charged into the metallic shell 30, thereby ensuring a seal between the outer surface of the sensor element 100 and the inner surface of the metallic shell 30.

A protector 24 made of metal is attached by welding to the outer circumferential surface of a forward end portion of the metallic shell 30 and covers a forward end portion of the sensor element 100 protruding from the forward end of the metallic shell 30. The protector 24 has a dual structure consisting of a closed-bottomed cylindrical outer protector 41 and closed-bottomed cylindrical inner protector 42 disposed within the outer protector 41.

Meanwhile, a forward end portion 25a of the outer casing 25 made of SUS430 is fitted to and fixed by laser welding or the like to a rear end portion of the metallic shell 30. The separator 50 is disposed within a rear portion of the outer casing 25. A fixing member 51 intervenes between the separator 50 and the outer casing 25. The fixing member 51 is engaged with a protrusion 50a of the separator 50, which will be described later, and is fixed between the outer casing 25 and the separator 50 by crimping the outer casing 25.

The separator 50 has insertion openings 50b extending therethrough rearward from its forward-end side. The insertion openings 50b partially accommodate the respective lead wires 11 to 14 and accommodate respective connection terminals 16 crimped to forward end portions of the lead wires 11 to 14.

The connection terminals 16 are electrically connected to respective electrode pads (electrode portions) 102 provided on a rear-end portion of the sensor element 100. The lead wires 11 to 14 are connected to an unillustrated external connector. Electrical signals are transmitted between the lead wires 11 to 14 and external equipment such as ECU through the connector.

Further, the rubber cep 52 having a generally circular columnar shape is disposed on the rear end side of the separator 50 for closing a rear-end opening portion 25b of the outer casing 25. In a state in which the rubber cap 52 is fitted into a rear end portion of the outer casing 25, the outer casing 25 is crimped radially inward along its outer circumference, whereby the rubber cap 52 is fixed to the outer casing 25. The rubber cap 52 also has second insertion holes 52b which extend therethrough between its forward end and rear end and through which the lead wires 11 to 14 are inserted.

Figure 2:
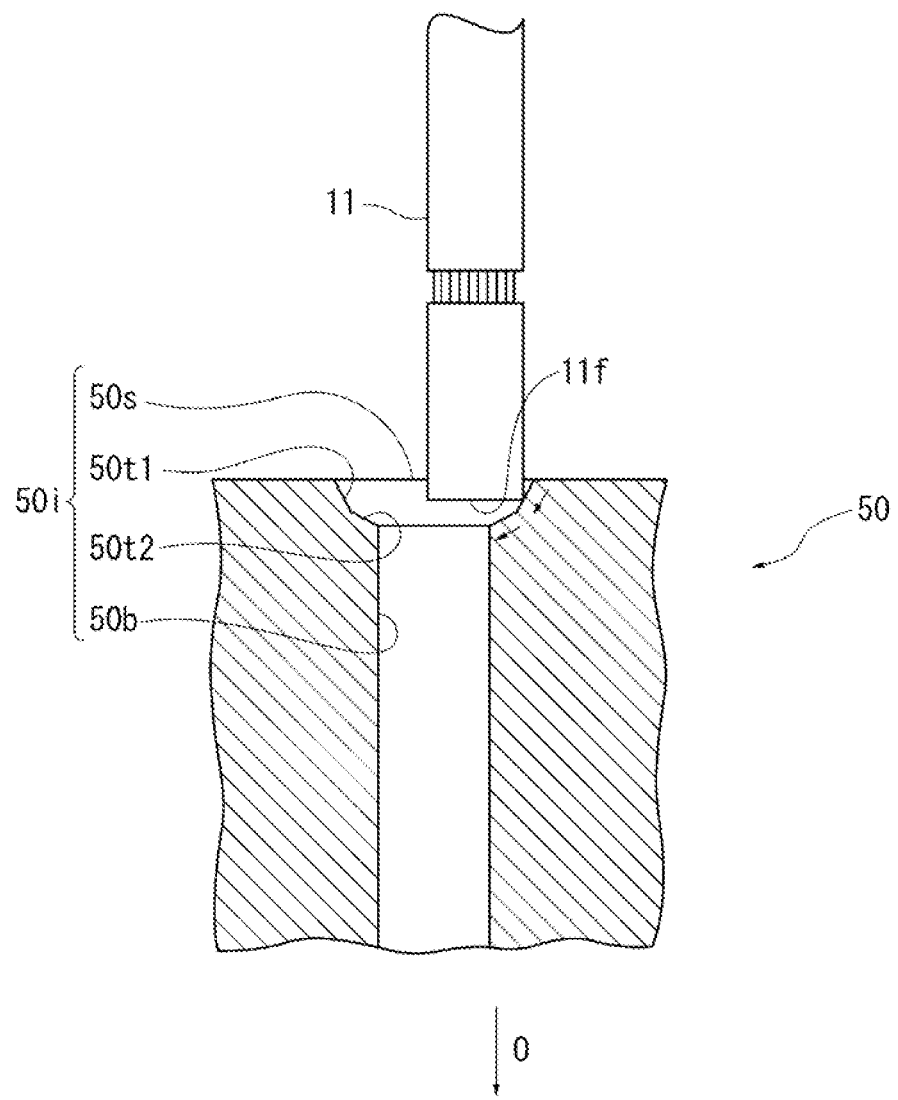
FIG. 2 is a sectional view showing a manner of insertion of a lead wire into the insertion section of a separator in a ceramic member unit according to the first aspect of the present invention.
Figure 3:
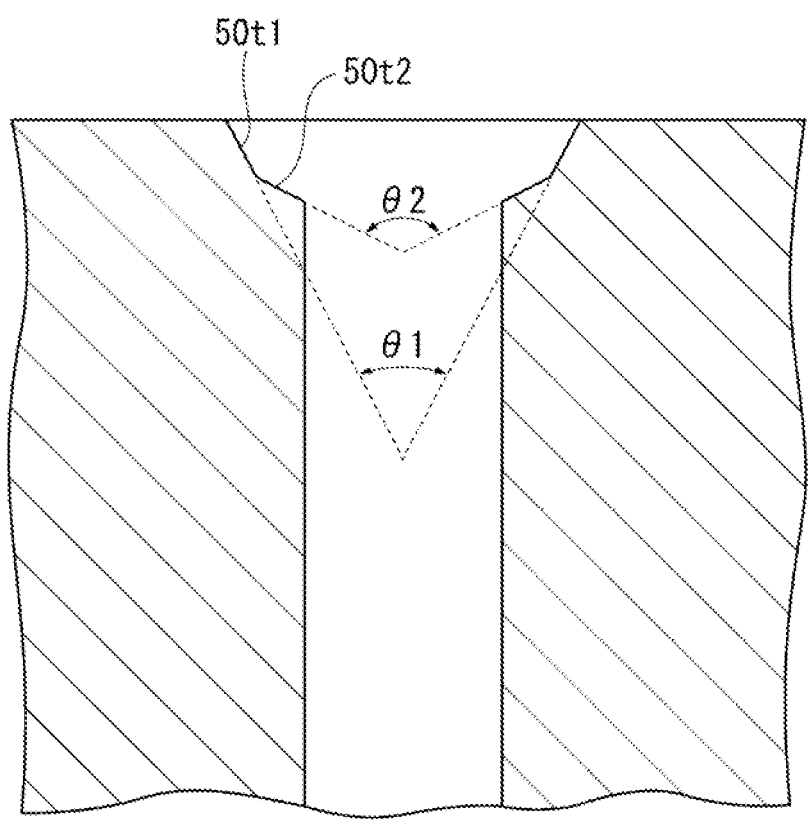
FIG. 3 is a view showing a taper angle.
Figure 4:
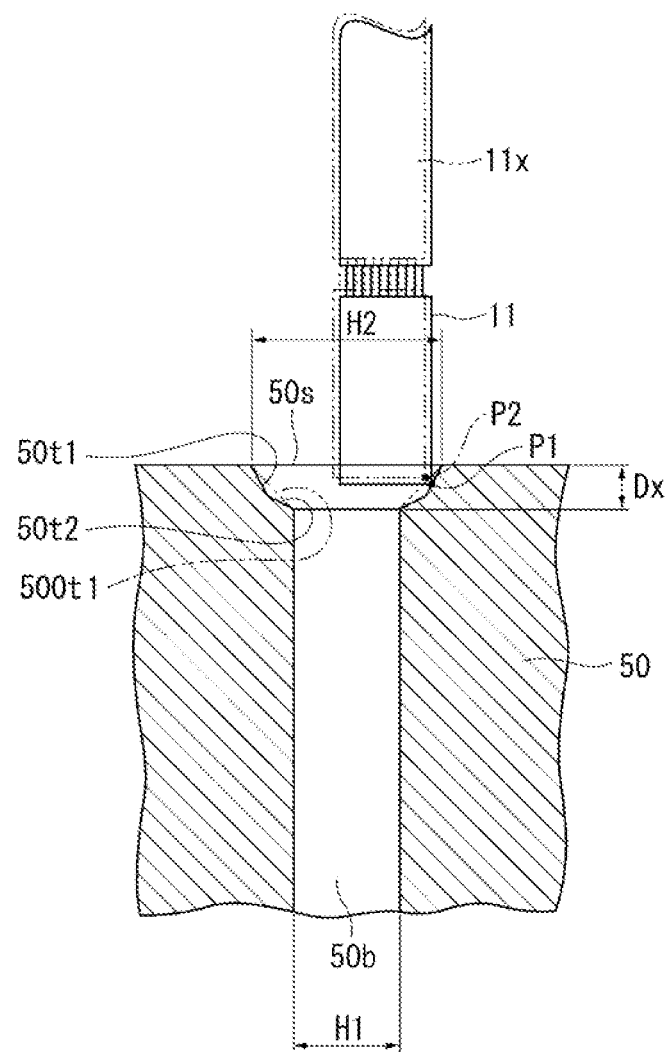
FIG. 4 is a sectional view showing insertability in inserting the lead wire of FIG. 2 into the insertion section of the separator.

Next, referring to FIGS. 2 to 4, the ceramic member unit according to the first aspect of the present invention will be described. FIG. 2 is a sectional view showing a manner of insertion of a lead wire 11, which corresponds to the insertion member of the ceramic member unit, into an insertion section 50i of a separator 50, which corresponds to the ceramic member. FIG. 3 is a view showing a taper angle. FIG. 4 is a sectional view showing insertability in inserting the lead wire 11 into the insertion section 50i of the separator 50.

As shown in FIG. 2, the separator 50 has the insertion section 50i which extends therethrough in the direction of the axial line O and into which the lead wire 11 is inserted. The insertion section 50i has an introduction opening 50s in a surface of the separator 50, and an insertion opening 50b which opens on a deeper side of the introduction opening 50s while communicating with the introduction opening 50s. The lead wire 11 can be inserted into the insertion opening 50b. In the present embodiment, the introduction opening 50s and the insertion opening 50b are square holes.

The insertion section 50i further has a two-step taper hole portion; namely, taper hole portions 50t1 and 50t2 in this order, in a region through which the introduction opening 50s and the insertion opening 50b communicate with each other. The taper hole portions 50t1 and 50t2 become narrower toward the insertion opening 50b. The taper hole portion 50t1 is connected to the introduction opening 50s, and the taper hole portion 50t2 is connected to the taper hole portion 50t1 and to the insertion opening 50b.

As shown in FIG. 3, a taper angle θ2 of the taper hole portion 50t2 is larger than a taper angle θ1 of the taper hole portion 50t1. Notably, the taper angle is an angle formed by tangents to taper surfaces in a cross section of the ceramic member (the separator 50) taken along an extending direction of the insertion section 50i (the direction of the axial line O).

Since the taper hole portions 50t1 and 50t2 increasing in taper angle toward the insertion opening 50b are connected to the insertion opening 50b, as shown in FIG. 4, the ease of insertion of the lead wire 11 into the insertion section 50i or the separator 50 improves.

Figure 9:
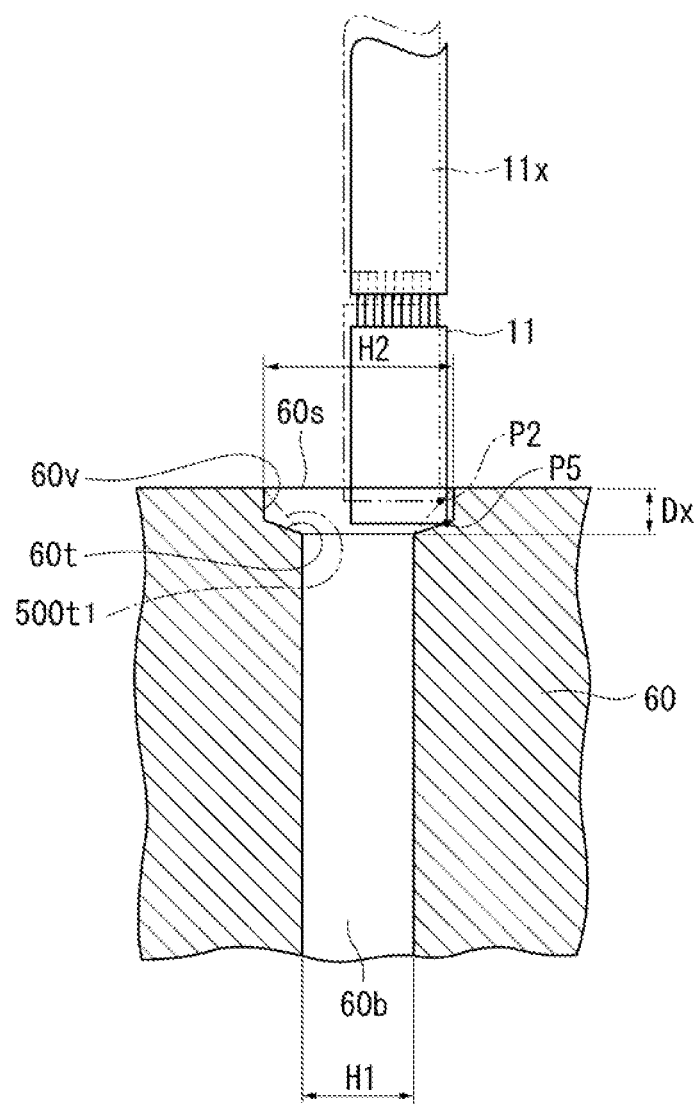
FIG. 9 is a sectional view showing insertability in inserting the lead wire of FIG. 8 into the insertion section of the separator.
Figure 10A:
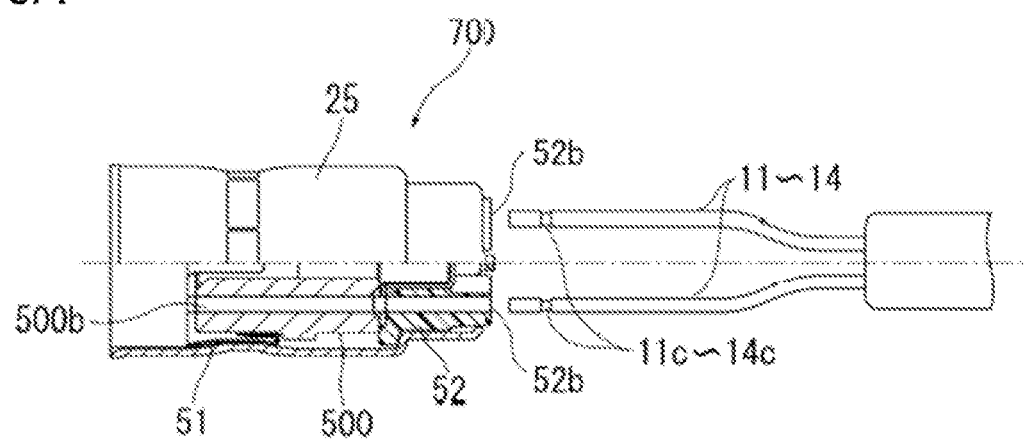
FIGS. 10A and 10B are views showing a method of manufacturing a conventional sensor.
Figure 10B:
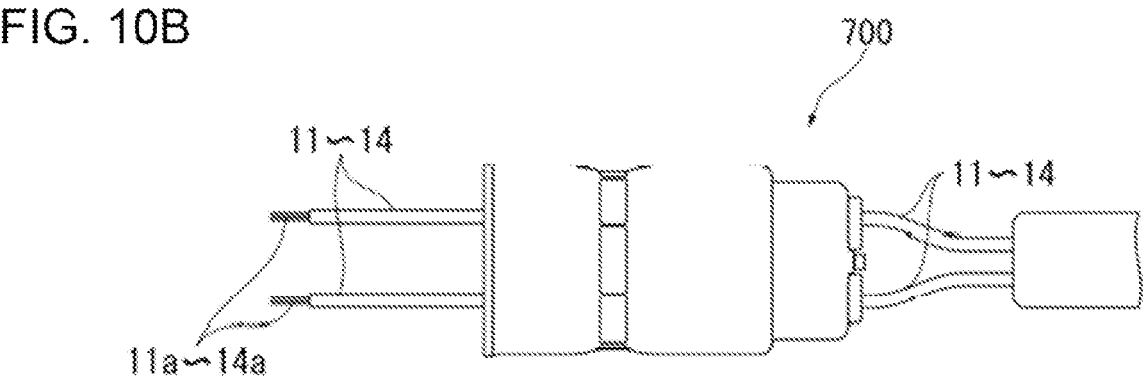
Figure 11A:
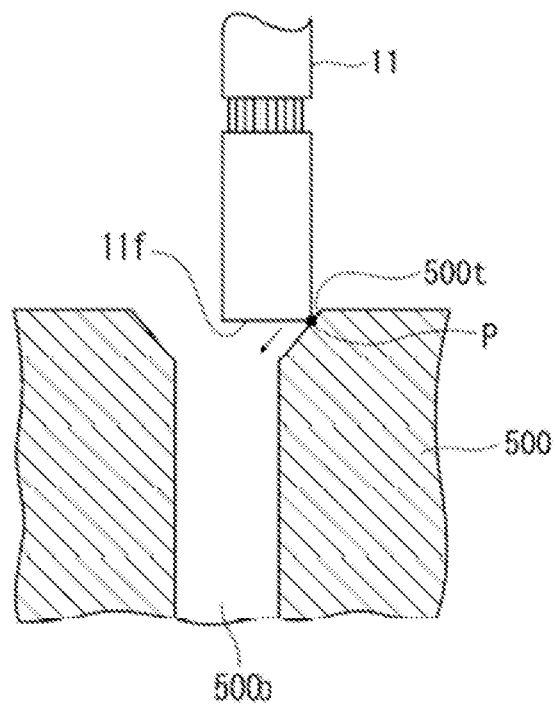
FIGS. 11A and 11B are sectional views showing a manner of insertion of a lead wire into the insertion section of a conventional separator.
Figure 11B:
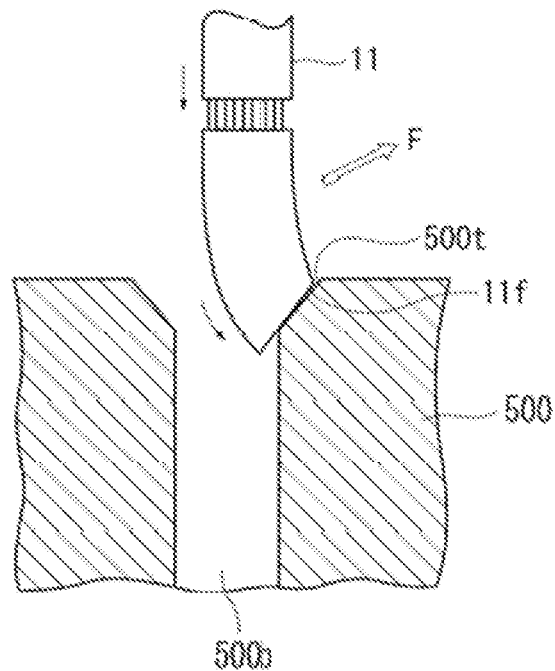
Figure 12:
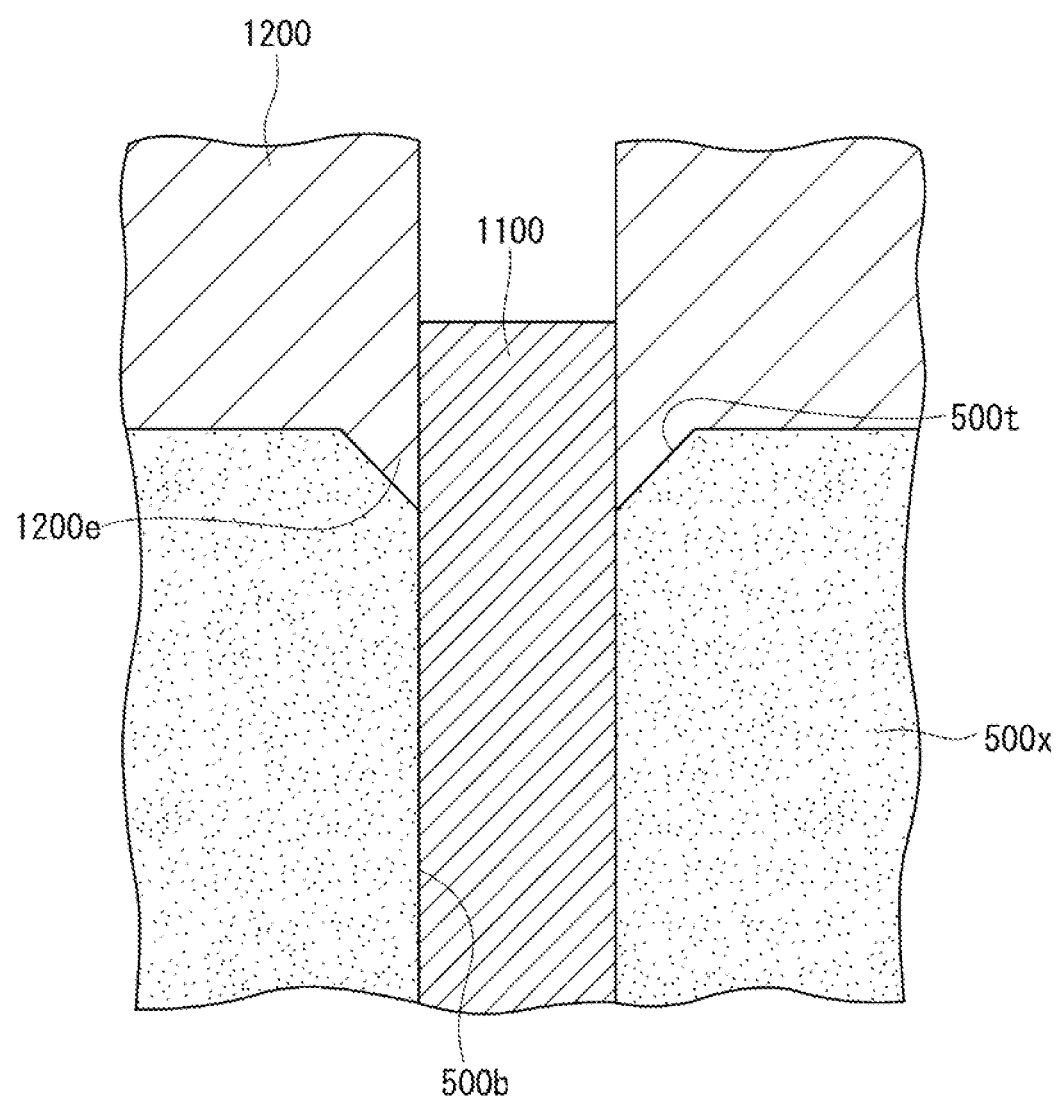
FIG. 12 is a sectional view showing a method of manufacturing the conventional separator.
Figure 13:
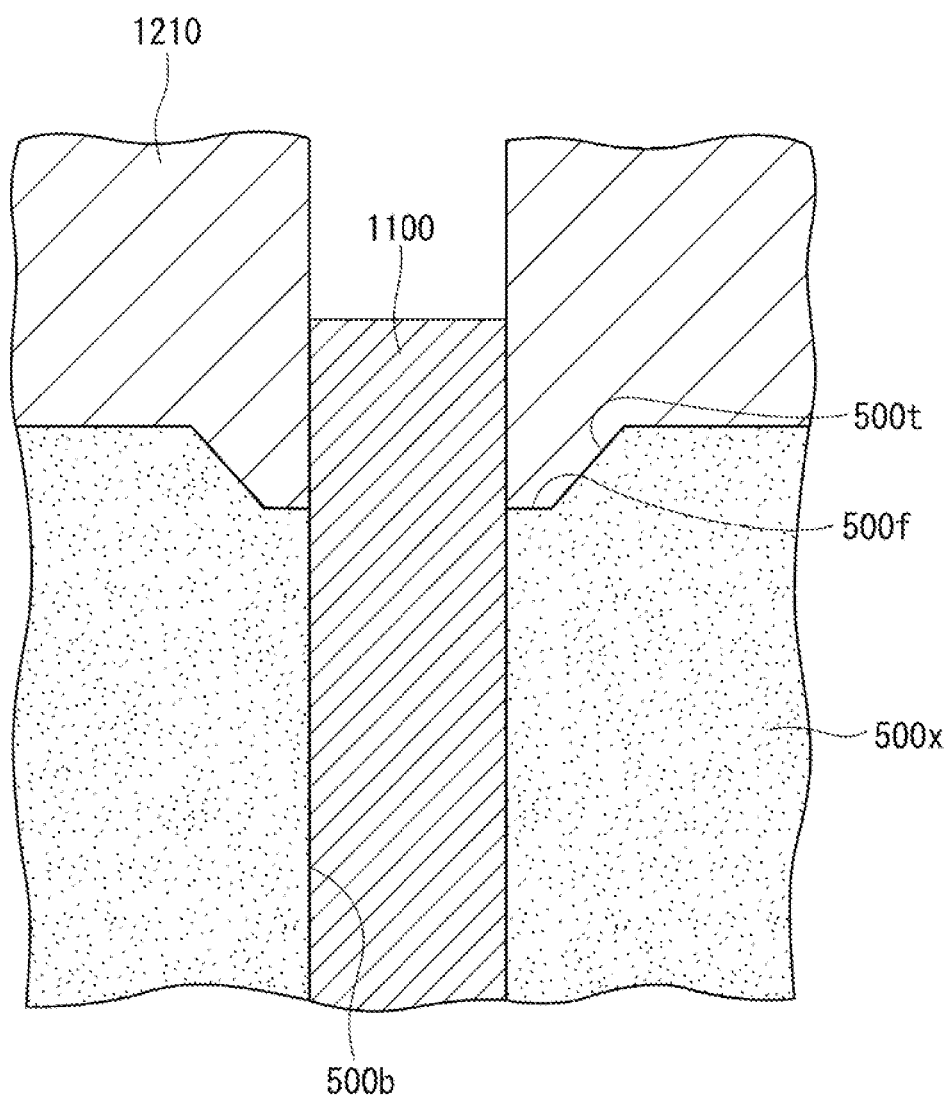
FIG. 13 is a sectional view showing a method of manufacturing another conventional separator.

In the case where the separator 50 is fixed in terms of the maximum diameter H2 of the introduction opening 50s, the maximum diameter H1 of the insertion opening 50b, and the depth Dx from the introduction opening 50s to the insertion opening 50b, a conventional one-step taper hole portion 500t1 as shown in FIG. 9 is represented by broken lines.

In the case where H1, H2, and Dx are fixed as mentioned above, the taper hole portions 50t1 and 50t2 which increase in taper angle toward the insertion opening 50b are always smaller (shallower) in taper angle than the one-step taper hole portion 500t1. That is, the taper hole portions 50t1 and 50t2 are always located radially outward of the taper hole portion 500t1.

Accordingly, when the lead wire 11 (11x) is inserted into the insertion section 50i of the separator 50, a distal end 11f of the lead wire 11 initially comes into contact with the taper hole portion 50t1 at a contact point P1 located more deeply (more closely to the insertion opening 50b) than a contact point P2 at which the distal end 11f of the lead wire 11x initially comes into contact with the taper hole portion 500t1. As a result, the lead wire 11 in a state (start state) in which the lead wire 11 has been inserted more deeply in the insertion section 50i is inserted further deeply. Therefore, even if the lead wire 11 bends to some extent, the lead wire 11 is restrained from slipping off to the outside from the insertion opening 50b and can be smoothly inserted further deeply into the insertion opening 50b, whereby insertability improves.

Figure 14:
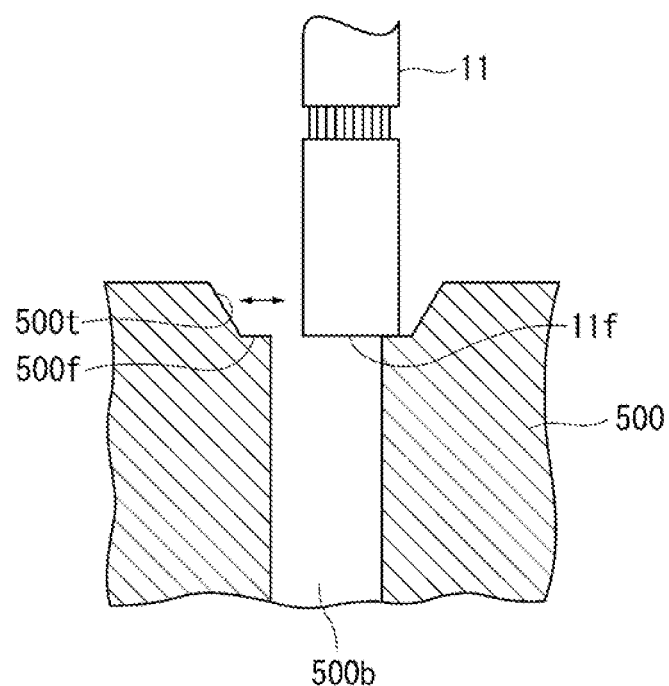
FIG. 14 is a sectional view showing a manner of insertion of a lead wire into the insertion section of the separator of FIG. 13.

The taper hole portion 50t1 guides the lead wire 11 toward the insertion opening 50b located radially inward, and, further, the taper hole portion 50t2 located mere deeply than the taper hole portion 50t1 is also tapered. Accordingly, as compared with the case where a horizontal portion 500f (see FIG. 14) is connected to the insertion opening 50b, the distal end. 11f of the lead wire 11 can be restrained from being caught.

Notably, an attempt to reduce. (shallow) the taper angle of the conventional one-step taper hole portion 500t1 requires a reduction in the maximum diameter H2 or an increase in the depth Dx. However, a reduction in the maximum diameter H2 causes difficulty in inserting the lead wire 11 into the insertion section 50i, and an increase in the depth Dx is limited by the shape, etc., of the separator 50 and causes deterioration in strength of the separator 50.

Figure 5:
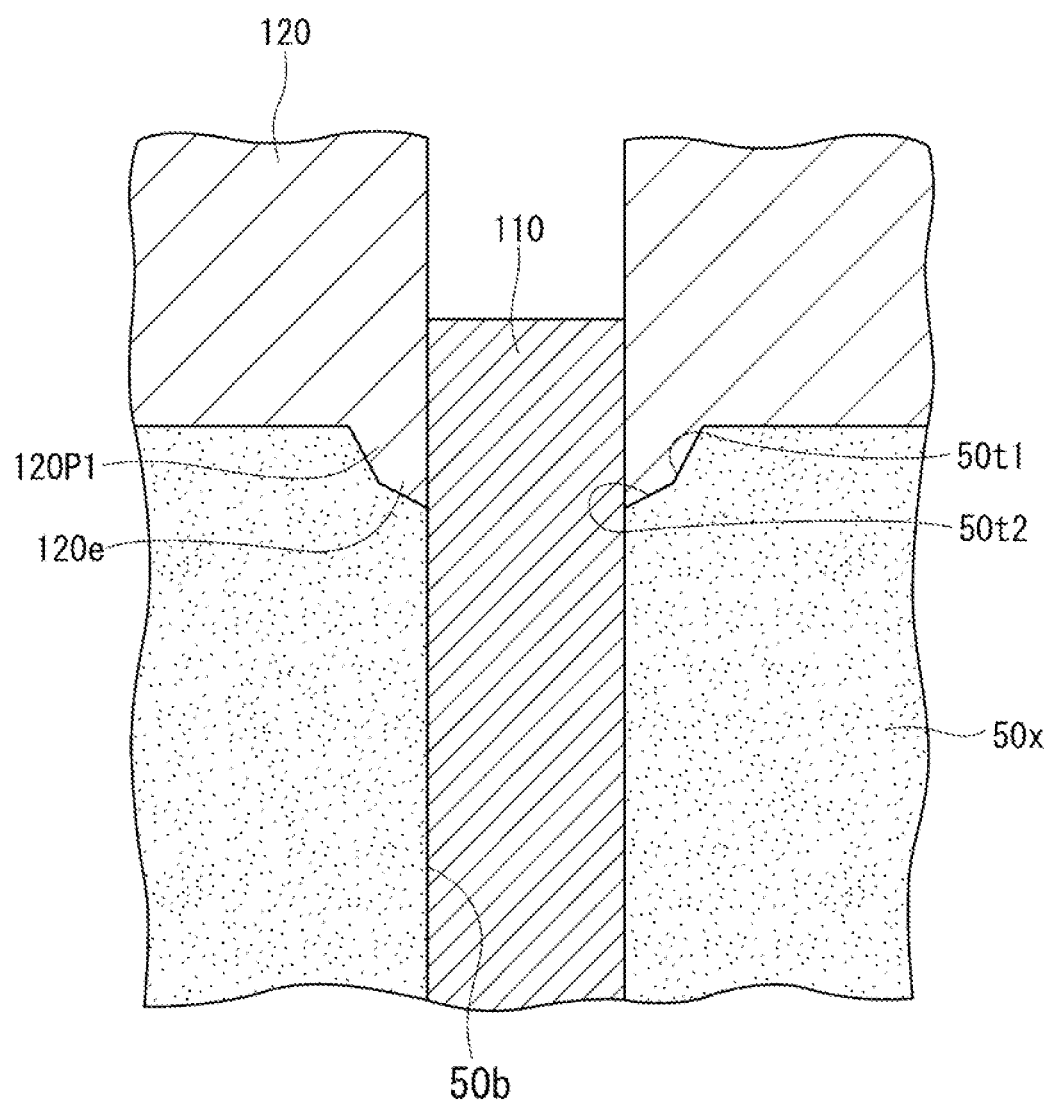
FIG. 5 is a sectional view showing a method of manufacturing the separator.

As shown in FIG. 5, in manufacture of the present separator, ceramic powder is pressed into a separator green compact 50x. In forming the green compact 50x by pressing, a pin 110 is inserted into the powder to form the insertion opening 50b, and a die 120 for forming the taper hole portions 50t1 and 50t2 is disposed around the pin and pressed. An edge portion 120e of the die 120 is less sharpened than a protrusion 120p1 adapted to form the taper hole portion 50t1. Accordingly, upon exposure to sliding movement of the die and compaction pressure of the powder, the edge portion 120e is unlikely to break, whereby productivity improves.

Figure 6:
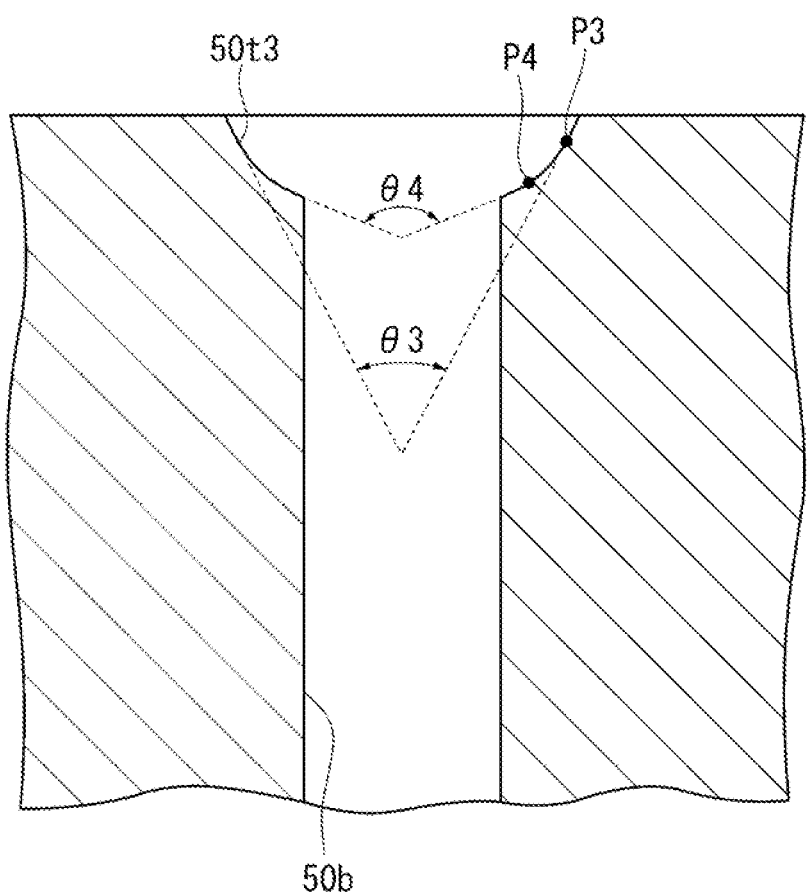
FIG. 6 is a view showing a modified separator in the ceramic member unit according to the first aspect of the present invention.

Notably, in addition to the above-mentioned two-step taper hole portion consisting of the taper hole portions 50t1 and 50t2, a taper hole portion whose taper angle increases toward the insertion opening may be a one-step taper hole portion 50t3 shown FIG. 6 whose taper surface is curved such that the taper angle changes smoothly.

In the case of the taper hole portion 50t3, as compared with a taper angle θ3 formed by tangents to its taper surface at a predetermined point P3, a larger taper angle θ4 is formed by tangents to its taper surface at a point P4 located more deeply (more closely to the insertion opening 50b) than the point P1.

Figure 7A:
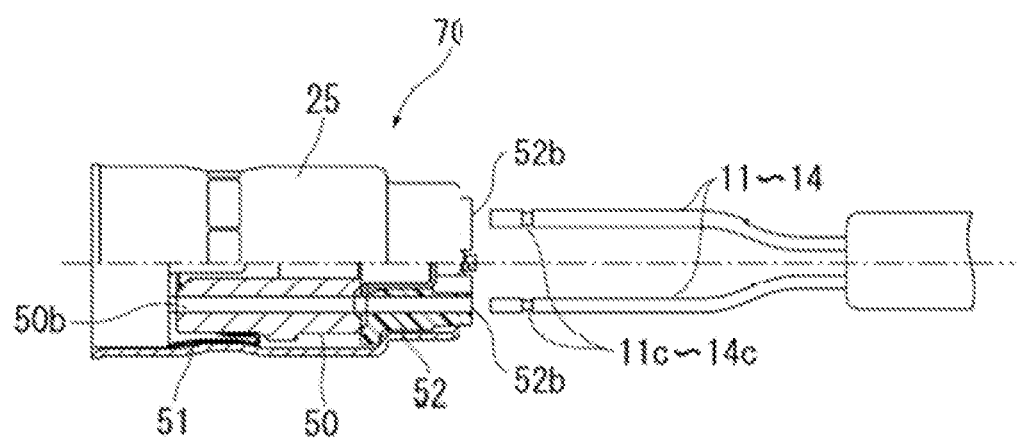
FIGS. 7A and 7B are views showing a method of manufacturing the sensor.
Figure 7B:
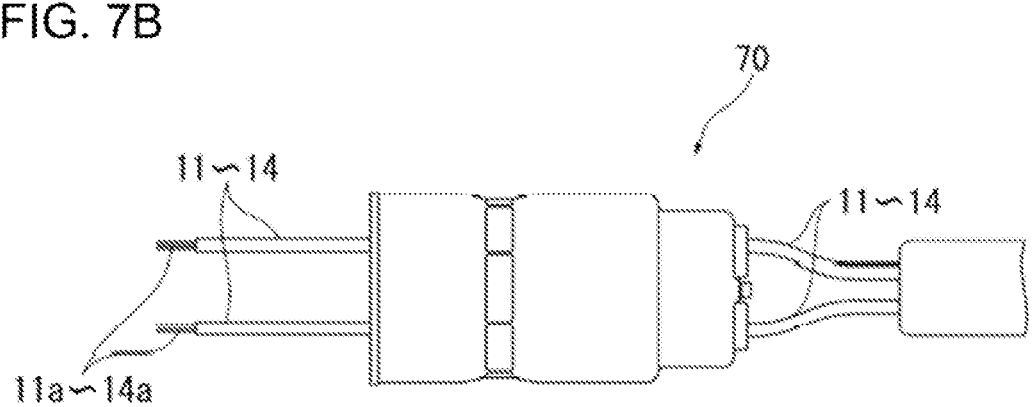

The sensor 1 can be manufactured as shown in FIGS. 7A and 7B. First, as shown in FIG. 7A, a sleeve unit 70 is assembled by sequentially fixing the separator 50 and the rubber cap 52 to the interior of an outer casing 25 from the forward-end side. Then, lead wires 11 to 14 are inserted from their distal ends into respective insertion openings 52b of the rubber cap 52 at the rear end of the sleeve unit 70 and then into respective insertion openings 50b of the separator 500.

Subsequently, as shown in FIG. 7B, covering materials located distally of cuts 11c to 14c are removed from distal ends of the lead wires 11 to 14 to expose core wires 11a to 14a. To the core wires 11a to 14a, unillustrated connection terminals are respectively connected by crimping. Next, the lead wires 11 to 14 are pulled rearward at their proximal side to accommodate the connection terminals in the insertion openings 50b, respectively, of the separator 50.

Further, the sleeve unit 70 with the lead wires 11 to 14 inserted therethrough is joined to an element unit (not shown) separately assembled beforehand, thereby completing the sensor 1.

Further, the sleeve unit 70 with the lead wires 11 to 14 inserted therethrough is joined to an element unit (not shown) separately assembled beforehand, thereby completing the sensor 1.

Figure 8:
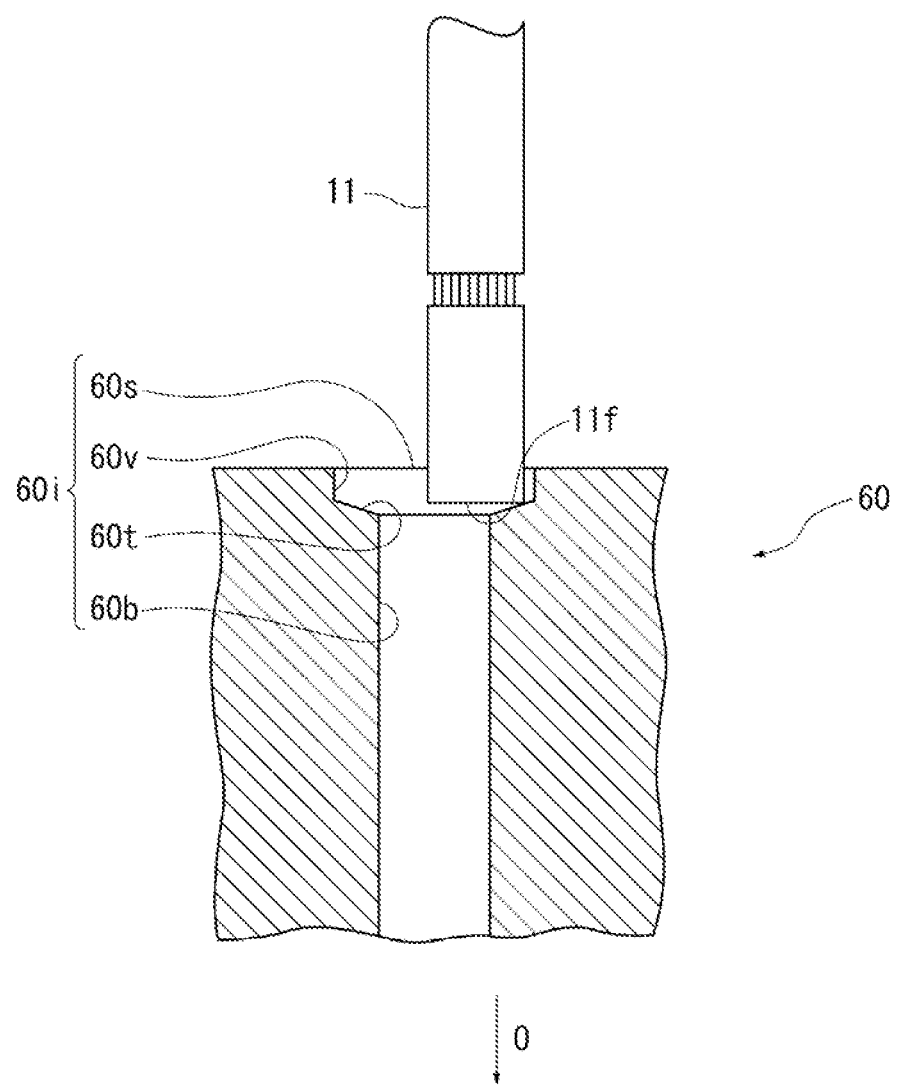
FIG. 8 is a sectional view showing a manner of insertion of a lead wire into the insertion section of a separator in a ceramic member unit according to the second aspect of the present invention.

Next, referring to FIGS. 8 and 9, a ceramic member unit according to the second aspect of the present invention will be described. FIG. 8 is a sectional view showing a manner of insertion of the lead wire 11 into an insertion section 60i of a separator 60. FIG. 9 is a sectional view showing insertability in inserting the lead wire 11 into the insertion section 60i of the separator 60.

Notably, the ceramic member unit according to the second aspect of the present invention includes the lead wire 11 and the separator 60, which correspond to the "insertion member" and the "ceramic member," respectively, in the claims.

As shown in FIG. 8, the separator 60 has the insertion section 60i which extends therethrough in the direction of the axial line O and into which the lead wire 11 is inserted. The insertion section 60i has an introduction opening 60s in a surface of the separator 60, and an insertion opening 60b which opens on a deeper aide of the introduction opening 60s while communicating with the introduction opening 60s. The lead wire 11 can be inserted into the insertion opening 60b. In the present embodiment, the introduction opening 60s and the insertion opening 60b are square holes.

The insertion section 60i further has a straight portion 60v and a deeper-wide taper hole portion 60t in this order from the introduction opening 60s side in a region through which the introduction opening 60s and the insertion opening 60b communicate with each other. The straight portion 60v is connected to the introduction opening 60s, and the deeper-side taper hole portion 60t is connected to the straight portion 60v and to the insertion opening 60b.

As a result of such a connection of the straight portion 60v and the deeper-side taper hole portion 60t to the insertion opening 60b, as shown in FIG. 8, the ease of insertion of the lead wire 11 into the insertion section 60i of the separator 60 improves.

Similarly to FIG. 4, in the case where the separator 60 is fixed in terms of the maximum diameter H2 of the introduction opening 60s, the maximum diameter H1 of the insertion opening 60b, and the depth Dx from the introduction opening 60s to the insertion opening 60b, the conventional one-step taper hole portion 500t1 as shown in FIG. 9 is represented by broken lines.

In the case where H1, H2, and Dx are fixed as mentioned above, the straight portion 60v is always located radially outward of the one-step taper hole portion 500t1, and the deeper-side taper hole portion 60t is always smaller (shallower) in taper angle than the taper hole portion 500t1. That is, the straight portion 60v and the deeper-side taper hole portion 60t are always located radially outward of the taper hole portion 500t1.

Accordingly, when the lead wire 11 (11x) is inserted into the insertion section 60i of the separator 60, the distal end 11$f$ of the lead wire 11 initially comes into contact with the deeper-side taper hole portion 60$t$ at a contact point P5 located more deeply (more closely to the insertion opening 60$b$) than the contact point P2 at which the distal end 11$f$ of the lead wire 11$x$ initially comes into contact with the taper hole portion 500$t$1. As a result, the lead wire 11 in a state (start state) in which the lead wire 11 has been inserted more deeply in the insertion section 60 is inserted further deeply. Therefore, even if the lead wire 11 bends to some extent, the lead wire 11 is restrained from slipping off to the outside from the insertion opening 60$b$ and can be smoothly inserted further deeply into the insertion opening 60$b$, whereby insertability improves.

Since the deeper-side taper hole portion 60$t$ guides the lead wire 11 toward the insertion opening 60$b$ located radially inward, and, further, the deeper-side taper hole portion 60$t$ is tapered, as compared with the case where a horizontal portion 500$f$ (see FIG. 14) is connected to the insertion opening 60$b$, the distal end 11$f$ of the lead wire 11 can be restrained from being caught.

It will be appreciated that the present invention is not limited to the embodiment described above and encompasses various modifications and equivalents within the spirit and scope of the present invention.

For example, no particular limitation is imposed on the shapes of the insertion member and the ceramic member and on members which serve as the insertion member and the ceramic member, as well as on the shapes of the introduction opening and the insertion opening.

The insertion opening is not required to be a through hole.

The sensor is not limited to a gas sensor, but may be, for example, a temperature sensor or the like.

DESCRIPTION OF REFERENCE NUMERALS

1: sensor
11 to 14: insertion member (lead wire)
50$b$, 60$b$: insertion opening
50$i$, 60$i$: insertion section
50$s$, 60$s$: introduction opening
50$t$1, 50$t$2: taper hole portion
50, 60: ceramic member (separator)
60$v$: straight portion
60$t$: deeper-side taper hole portion
100: sensor element
O: axial line

The invention claimed is:

1. A sensor comprising at least:
an insertion member and
a ceramic member having an insertion section into which the insertion member is inserted;
the sensor being characterized in that
the insertion section has at least an insertion opening which opens on a deeper side of an introduction opening in a surface of the ceramic member while communicating with the introduction opening and into which the insertion member can be inserted;
the insertion section further has a taper hole portion in a region through which the introduction opening and the insertion opening communicate with each other, the taper hole portion becoming narrower toward the insertion opening; and
the taper hole portion is connected to the insertion opening while increasing in taper angle toward the insertion opening,
wherein the insertion section forms a through hole extending from the insertion opening toward a deeper side, and
wherein the sensor further comprises a sensor element extending in a direction of an axial line, the ceramic member is a separator, and the insertion member is a lead wire electrically connected to the sensor element.

2. A sensor comprising at least:
an insertion member and
a ceramic member having an insertion section into which the insertion member is inserted;
the sensor being characterized in that
the insertion section has at least an insertion opening which opens on a deeper side of an introduction opening in a surface of the ceramic member while communicating with the introduction opening and into which the insertion member can be inserted;
the insertion section further has a straight portion and a deeper-side taper hole portion in this order from the introduction opening in a region through which the introduction opening and the insertion opening communicate with each other;
the straight portion extends from the introduction opening toward the insertion opening; and
the deeper-side taper hole portion is connected to the insertion opening while becoming narrower from the straight portion toward the insertion opening,
wherein the insertion section forms a through hole extending from the insertion opening toward a deeper side, and
wherein the sensor further comprises a sensor element extending in a direction of an axial line, the ceramic member is a separator, and the insertion member is a lead wire electrically connected to the sensor element.

* * * * *